US007532928B2

United States Patent
Lang (10) Patent No.: US 7,532,928 B2
(45) Date of Patent: May 12, 2009

(54) ATRIAL DEFIBRILLATOR

(75) Inventor: Volker Lang, West Linn, OR (US)

(73) Assignee: Biotronik CRM Patent AG (DE)

( * ) Notice: Subject to any disclaimer, the term of this patent is extended or adjusted under 35 U.S.C. 154(b) by 537 days.

(21) Appl. No.: 11/354,713

(22) Filed: Feb. 15, 2006

(65) Prior Publication Data

US 2007/0191889 A1 Aug. 16, 2007

(51) Int. Cl.
*A61N 1/08* (2006.01)
*A61N 1/39* (2006.01)
*A61N 1/37* (2006.01)

(52) U.S. Cl. .................. 607/5; 607/4; 607/25
(58) Field of Classification Search ............ 607/4, 607/5, 7, 8, 25
See application file for complete search history.

(56) References Cited

U.S. PATENT DOCUMENTS

| 5,282,836 | A | 2/1994 | Kreyenhagen et al. | |
|---|---|---|---|---|
| 5,350,402 | A | 9/1994 | Infinger et al. | |
| 5,411,524 | A | 5/1995 | Rahul | |
| 5,828,837 | A | 10/1998 | Eikeland | |
| 6,149,601 | A | 11/2000 | Bonnet et al. | |
| 6,512,951 | B1 | 1/2003 | Marcovecchio et al. | |
| 6,629,931 | B1 * | 10/2003 | Begemann et al. | 600/508 |
| 6,754,528 | B2 * | 6/2004 | Bardy et al. | 607/5 |
| 2003/0009200 | A1 | 1/2003 | Noren et al. | |
| 2004/0172080 | A1 * | 9/2004 | Stadler et al. | 607/17 |

FOREIGN PATENT DOCUMENTS

EP 0908196 A1 4/1999

OTHER PUBLICATIONS

Ayers et al., Ventricular Proarrhythmic Effects of Ventricular Cycle Length and Shock Strength in a Sheep Model of Transvenous Atrial Defibrillation; Circulation Journal; Jan. 1994; pp. 413-422; vol. 89, No. 1; U.S.A.

* cited by examiner

*Primary Examiner*—Carl H. Layno
*Assistant Examiner*—Tammie K. Heller
(74) *Attorney, Agent, or Firm*—Hahn Loeser & Parks LLP (57) ABSTRACT

An atrial defibrillator has a stimulation pulse generator to generate pacing pulses, a sensing stage for sensing intrinsic ventricular events, (an R-wave having an amplitude). It also includes a defibrillation shock generator to generate an atrial defibrillation shock, an atrial fibrillation detector adapted to detect an atrial fibrillation, and a control unit connected to the stimulation pulse generator. The sensing stage, the atrial fibrillation detector, the defibrillation shock generator, and control unit are adapted to trigger an atrial defibrillation shock after detection of an atrial fibrillation and synchronous with a sensed or a paced ventricular event. The control unit is adapted to compare a sensed R-wave amplitude with a reference R-wave amplitude and synchronize an atrial defibrillation shock with a paced ventricular event or a sensed ventricular event if the sensed ventricular event is an R-wave having an amplitude of at least 60% of the magnitude of the reference amplitude.

17 Claims, 3 Drawing Sheets

ATRIAL DEFIBRILLATOR

FIELD OF INVENTION

The present invention generally relates to an atrial defibrillator for delivering an atrial defibrillation shock to an atrium of a heart suffering from atrial fibrillation (AF). The atrial defibrillator preferably is an implantable cardioverter/defibrillator (ICD) that also provides for basic or sophisticated pacing functionality of a dual or more chamber implantable pacemaker. In particular, the invention relates to an atrial defibrillator capable of delivering an atrial defibrillation shock synchronous to a ventricular contraction.

The atrial defibrillator comprises at least one stimulation pulse generator to generate pacing pulses for at least a ventricle of a heart. Further, the atrial defibrillator comprises at least one sensing stage for sensing of intrinsic ventricular events, said intrinsic ventricular event being an R-wave having an amplitude with a measured magnitude. The atrial defibrillator further comprises an atrial shock generator to generate an atrial defibrillation shock and an atrial fibrillation detector adapted to detect an atrial fibrillation. A control unit connected to the stimulation pulse generator, the sensing stage, the atrial fibrillation detector and the fibrillation shock generator is adapted to trigger an atrial defibrillation shock after detection of an atrial fibrillation synchronous with a sensed or paced ventricular event.

BACKGROUND OF THE INVENTION

Fibrillation is a particular form of tachycardia that may occur as well in an atrium (atrial fibrillation) as in a ventricle (ventricular fibrillation) of a heart. Other forms of tachycardia are, for example, flutter. A tachycardia is characterized by a rapid heart rate. Typically, fibrillation is characterized by a very high rate of contraction of the heart chamber (atrium or ventricle) affected and of very low amplitude of the sensed electrical potential. Typically, during an episode of fibrillation, no coordinated contraction of the whole heart chamber occurs but only a circulating excitation of the myocardium wherein only one part of the heart chamber's muscle (the myocardium) is excited (depolarised) and thus contracted, whereas other parts of the myocardium already are repolarised and thus relaxed. Therefore, during episodes of fibrillation, the affected heart chamber is unable to efficiently pump blood. For this reason, a ventricular fibrillation (VF) usually is lethal if not treated within minutes or seconds. On the other hand, an atrial fibrillation usually is not life threatening, since the atrial contraction only contributes to a smaller part to the total pumping power of the heart that is typically expressed as an minute volume: pumped blood volume per minute.

A typical treatment of a fibrillation is the delivery of a defibrillation shock to the fibrillating heart chamber. A defibrillation shock usually has a much higher intensity than for example a stimulation or pacing pulse. The intensity of a defibrillation shock shall be sufficient to render the whole myocardium of the fibrillating heart chamber refractory in order to interrupt a circulating excitation of the myocardium and thus to synchronize the contraction of the myocardium of the heart chamber in all it's parts.

Even though atrial fibrillation or atrial flutter is not life threatening, there are several reasons for treating atrial fibrillation, although such treatment is painful for the patient. One reason is that the atrial fibrillation my lead to lethal ventricular fibrillation. Also, atrial fibrillation is compromising the heart's performance because of the loss of atrioventricular synchrony associate with an atrial fibrillation and can cause discomfort as for example, fatigue.

An atrial defibrillation shock for treatment of an atrial fibrillation usually is applied by means of intraatrial shock electrodes. When an atrial defibrillation shock is delivered at the wrong point of time during a heart cycle, the atrial defibrillation itself can cause a ventricular fibrillation. Therefore, delivery of the atrial defibrillation shock during the so-called vulnerable phase of the ventricle is to be avoided. For this reason, it has become common in the art to deliver the atrial defibrillation shock synchronously with a ventricular contraction which also is called a ventricular event. Such ventricular event may be the sensed event in case of a natural (intrinsic) contraction of the ventricle or a paced event, if the contraction of the ventricle is caused by a ventricular stimulation pulse.

U.S. Pat. No. 5,282,836 for example, the disclosure of which is hereby incorporated by reference herein, discloses an atrial defibrillator capable of providing pre-cardioversion pacing. By such pre-cardioversion pacing, the ventricle is stimulated with a fixed pacing rate for a determined number of cardiac cycles in order to establish a stable ventricular rhythm to which the atrial defibrillation shock can be synchronized with.

Further prior art documents dealing with the problem of synchronizing an atrial defibrillation shock with the ventricular rhythm are, for example, U.S. Pat. Nos. 5,282,837 and 6,512,951, the disclosures of which are hereby incorporated by reference herein.

SUMMARY OF THE INVENTION

It is an aspect of the present invention to provide an atrial defibrillator allowing reliable synchronization of an atrial defibrillation shock with a ventricular contraction.

According to the invention this aspect is achieved by an atrial defibrillator having a control unit that is adapted to compare a sensed R-wave amplitude with a reference R-wave amplitude and synchronize an atrial defibrillation shock with either a paced ventricular event or a sensed ventricular event if said sensed ventricular event is an R-wave having an amplitude of at least 60% of the magnitude of said reference amplitude.

The invention is based on the insight that in some cases, the sensed signal characterizing a ventricular repolarisation—a T-wave—is misinterpreted as R-wave. If an atrial defibrillation shock is synchronized with a T-wave instead of an R-wave, there is a serious risk of inducing a ventricular fibrillation since the T-wave occurs during the vulnerable phase of the myocardium. In order to avoid such misinterpretation of a T-wave as an R-wave, a criterion for discriminating T-waves from R-waves is introduced, the criterion being an amplitude criterion.

In order to monitor the heart chamber and thus to determine whether or not a natural contraction of a heart chamber has occurred, a pacemaker has a sensing stage which during operation of the pacemaker is connected to an electrode placed in a respective heart chamber. A natural contraction of a heart chamber can be detected by evaluating electrical potentials sensed by such sensing electrode. In the sensed electrical signal, the depolarization of an atrium muscle tissue is manifested by occurrence of a signal known as "P-wave". Similarly, the depolarization of ventricular muscle tissue is manifested by the occurrence of a signal known as "R-wave". A P-wave or an R-wave represent a sensed atrial event or a sensed ventricular event, respectively, in the further course of this application.

An atrial sensing stage senses P-waves as sensed atrial events As, a ventricular sensing stage senses R-waves (sensed ventricular events Vs) and T-waves. The atrial sensing stage may be connected to an atrial fibrillation detector which is adapted to detect an atrial fibrillation by evaluating the atrial sense signal generated by the atrial sensing stage. Criteria for detection of atrial fibrillation are a high atrial rate (high frequency of atrial sensed events) and a low amplitude of sensed P-waves. Criteria for detection of atrial fibrillation are well known in the art.

Sensing stages usually include bandpass-filters to pre-process the electrical signals received by an intracardiac sensing electrodes.

One purpose of these filters is to eliminate noise from the sensed signal.

In a preferred embodiment, the ventricular sensing stage for sensing R-waves has a bandpass-filter with a passband from 15 to 80 Hertz. Such bandpass-filter is suitable to reduce the T-wave amplitude as compared to the R-wave amplitude. Thus, the ventricular sensing stage is less susceptible to wrongly sensed T-waves as R-waves.

Regarding synchronization of an atrial defibrillation shock with a sensed R-wave, it is preferred if the atrial defibrillation shock is delivered within 30-100 ms after detection of an R-wave having an amplitude with a magnitude of at least 60% of the magnitude of the referent amplitude. A time interval of <100 ms is considered to be short enough to avoid delivery of the atrial defibrillation shock during the vulnerable phase of the ventricle.

In order to determine a suitable reference amplitude, the atrial defibrillator comprises a memory for storing sampled R-wave amplitudes sensed during episodes of sinus rate. A sinus rate is present, if no ventricular or atrial tachycardia (including flutter and fibrillation) is present. Thus, only R-wave amplitudes measured in absence of any tachycardia are stored in the memory. The control unit preferably is adapted to access the memory and to generate a mean value from R-wave amplitude values stored in said memory and to use the mean amplitude value as a reference amplitude.

In order to more reliably detect an R-wave, the ventricular sensing stage preferably comprises a second filter having a lower cut of frequency of 22 to 26 Hertz, i.e a bandpass-filter having a pass band between 24 and 80 Hz. This allows more specific detection of R-waves.

The first filter having a pass band from 15 to 80 Hz and the second filter having a pass band from 24 to 80 Hz may be switched in parallel to each other so that they are permanently operational or they may be switchably connected to the control unit. In the latter case, the control unit is adapted to switch back and forth between the two filters depending on the operational state of the atrial defibrillator.

Regarding synchronization of an atrial defibrillation shock with a sensed R-wave, it is preferred if the atrial defibrillation shock is delivered within 30-100 ms after detection of an R-wave synchronously detected by the first and second bandpass-filter and having an amplitude with a magnitude of at least 60% of the magnitude of the referent amplitude, measured with the second bandpass-filter. A time interval of <100 ms is considered to be short enough to avoid delivery of the atrial defibrillation shock during the vulnerable phase of the ventricle.

In order to determine a suitable reference amplitude the atrial defibrillator comprises a memory for storing sampled R-wave amplitudes sensed during episodes of sinus rate. A sinus rate is present, if no ventricular or atrial tachycardia (including flutter and fibrillation) is present. Thus, only R-wave amplitudes measured in absence of any tachycardia are stored in the memory. The control unit preferably is adapted to access the memory and to generate a mean value from R-wave amplitude values stored in said memory and to use the mean amplitude value as a reference amplitude.

Preferably, the ventricular signal filtered by the bandpass-filter having a pass band between 24 and 80 Hz is used for storing in said memory.

In order to more reliably detect ventricular contractions and thus to confirm an R-wave, the atrial defibrillator preferably comprises an impedance sensor connected to an impedance evaluation unit which is adapted to detect ventricular contractions by evaluating an intracardiac impedance signal. This allows for detection of mechanical contraction of the ventricle and thus a confirmation of a depolarisation of the myocardium.

In a preferred embodiment, the control unit is connected to the impedance evaluation unit and is adapted to evaluate an actual intracardiac impedance signal by comparing said actual intracardiac impedance signal with a stored reference intracardiac impedance signal. Preferably, the control unit is further adapted to form a difference area between an actual impedance signal and a stored reference impedance signal and to compare the difference area to a stored reference area, said stored reference area representing the area defined by the reference impedance signal.

For the purpose of reliable confirmation of a ventricular contraction and to avoid synchronization of the atrial defibrillation shock with a T-wave wrongly sensed as R-wave, the control unit is preferably adapted to evaluate the intracardiac impedance signal in a time window starting with a sensed ventricular event (which should be an R-wave but also could be a T-wave wrongly sensed as R-wave) and ending after 30 to 100 ms and to suppress delivery of an atrial defibrillation shock when the difference area is larger than 10 to 20% of the reference area.

Preferably, the control unit suppresses delivery of an atrial defibrillation shock when the difference area is larger than 15% of the reference area.

In addition to being an atrial defibrillator, a preferred implantable medical device comprises all components of an advanced dual chamber demand pacemaker. These components in particular may include atrial and ventricular sensing stages and atrial and ventricular stimulation pulse generators. Furthermore, the implantable medical device (atrial defibrillator/pacemaker) comprises an activity sensor to allow for rate adaptive pacing with a pacing rate matching the hemodynamic demand.

In a dual chamber (or more) demand-type pacemaker/atrial defibrillator, intracardiac electrodes (electrode suitable for placement in an heart chamber, in particular the right ventricle and the right atrium of a heart) are coupled through intravenous and/or epicardial leads to sensing stages (sense amplifiers having a band pass filter characteristic providing some adjustable gain for amplification of sensed signals) housed in an implanted pacemaker. Electrical activity (changes of sensed electrical potentials caused by depolarization/repolarization of the myocardium) occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing.

Separate stimulation pulse generators are usually provided for each heart chamber (atrium or ventricle) to be stimulated.

The control unit triggers the generation of a respective atrial or ventricular stimulation pulse according to a pre-programmed, variable timing regime in order to provide for adequate timing of the stimulation pulses.

A stimulation pulse to the myocardium may cause a contraction of a respective heart chamber, if the myocardium of that chamber is not in a refractory state and if the stimulation pulse has an intensity above the stimulation threshold of said myocardium.

Depending on the mode of operation, a pacemaker only delivers a stimulation pulse (pacing pulse) to a heart chamber (atrium or ventricle) if needed, that is, if no natural contraction of that chamber occurs. Such mode of operation is called an inhibited or demand mode of operation since the delivery of a stimulation pulse is inhibited if a natural contraction of the heart chamber is sensed within a predetermined time interval (usually called escape interval) so the heart chamber is only stimulated if demanded.

In a demand mode, the pacemaker/atrial defibrillator monitors the heart chamber to be stimulated in order to determine if a cardiac contraction (heartbeat) has naturally occurred. Such natural (non-stimulated) contraction, also referred to as "intrinsic" or "signs" cardiac activity, are manifested by the occurrence of recognizable electrical signals that accompany the depolarization or contraction of a cardiac muscle tissue (myocardium). The depolarization of the myocardium immediately precedes a cardiac contraction. For the purpose of the present application, depolarization and contraction may be considered as simultaneous events and the terms "depolarization" and "contraction" are used herein as synonyms.

In a demand mode of operation, the pacemaker/atrial defibrillator monitors the heart for the occurrence of P-waves and/or R-waves. If such signals are sensed within a prescribed time period or time window, which is called atrial or ventricular escape interval, respectively, then the escape interval is reset (i.e., restarted) and generation of a stimulation pulse is inhibited and no unnecessary stimulation pulse is triggered. The escape interval is measured from the last heartbeat, i.e., from the last occurrence of an intrinsic (sensed) atrial event (P-wave, A-sense, $A_S$) if the atrium is monitored, or an intrinsic (sensed) ventricular event (R-wave, V-sense, $V_S$) if the ventricle is monitored, or the generation of a stimulation pulse (V-pace, $V_P$; A-pace, $A_P$) if no respective intrinsic event has occurred. If the escape interval "times-out," i.e., if a time period equal to the escape interval has elapsed without the sensing of a P-wave and/or R-wave (depending upon which chamber of the heart is being monitored), then a stimulation pulse is generated at the conclusion of the escape interval, and the escape interval is reset, i.e., restarted. In this way, the pacemaker provides stimulation pulses "on demand," i.e., only as needed, when intrinsic cardiac activity does not occur within the prescribed escape interval.

Several modes of operation are available in a state of the art multi-mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

Multiple-mode, demand-type, cardiac pacemakers shall allow a sequence of contractions of the heart's chamber which equals as far as possible a natural behavior of the healthy heart for damaged or diseased hearts that are unable to do so on their own In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the atrium contracts and forces the blood that has accumulated therein into the ventricle. The natural stimulus causing the atrium to contract is conducted to ventricle via the atrioventricular node (AV node) with a short, natural delay, the atrioventricular delay (AV-delay). Thus a short time after an atrial contraction (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 60 ms; a typical time interval between contraction of the ventricle and the next contraction of the atrium might be 800 ms. Thus, it is an atrial contraction (A), followed a relatively short time thereafter by a ventricle contraction (V), followed a relatively long time thereafter by the next atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the ventricle is contracting when it is not filled with blood).

To mimic the natural behavior of a heart, a dual-chamber pacemaker, in conventional manner, defines a basic atrial escape interval (AEI) that sets the time interval between a ventricular event and an atrial event; as well as a basic AV delay (AVD) or ventricular escape interval (VEI) that sets the time interval or delay between an atrial event and a ventricular event. For the purpose of this application, a "ventricular event" may refer either to a natural ventricular contraction (intrinsic ventricular event) which is sensed as an R-wave or to a ventricular stimulation pulse (V-pulse, $V_P$). Similarly, an atrial event shall refer to both, a P-wave or an atrial stimulation pulse (A-pulse, $A_P$). The AEI and AVD (or VEI) thus a length of a heart cycle which is reciprocal to the pacing rate at which stimulation pulses are generated and delivered to a patient's heart in the absence of sensed natural cardiac activity. In a demand-type pacemaker, these electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing.

In a preferred embodiment of the invention, the atrial defibrillator is part of an implantable medical device that is adapted to also provide the pacing modes disclosed above since pacing of the ventricle may be necessary to stabilize the ventricular rhythm in order reliably synchronize the atrial defibrillation shock with a ventricular contraction.

To be able to treat even more complex heart failures, the implantable medical device including the atrial defibrillator may comprise means for ventricular defibrillation and/or means for left ventricular stimulation in addition to right ventricular stimulation.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
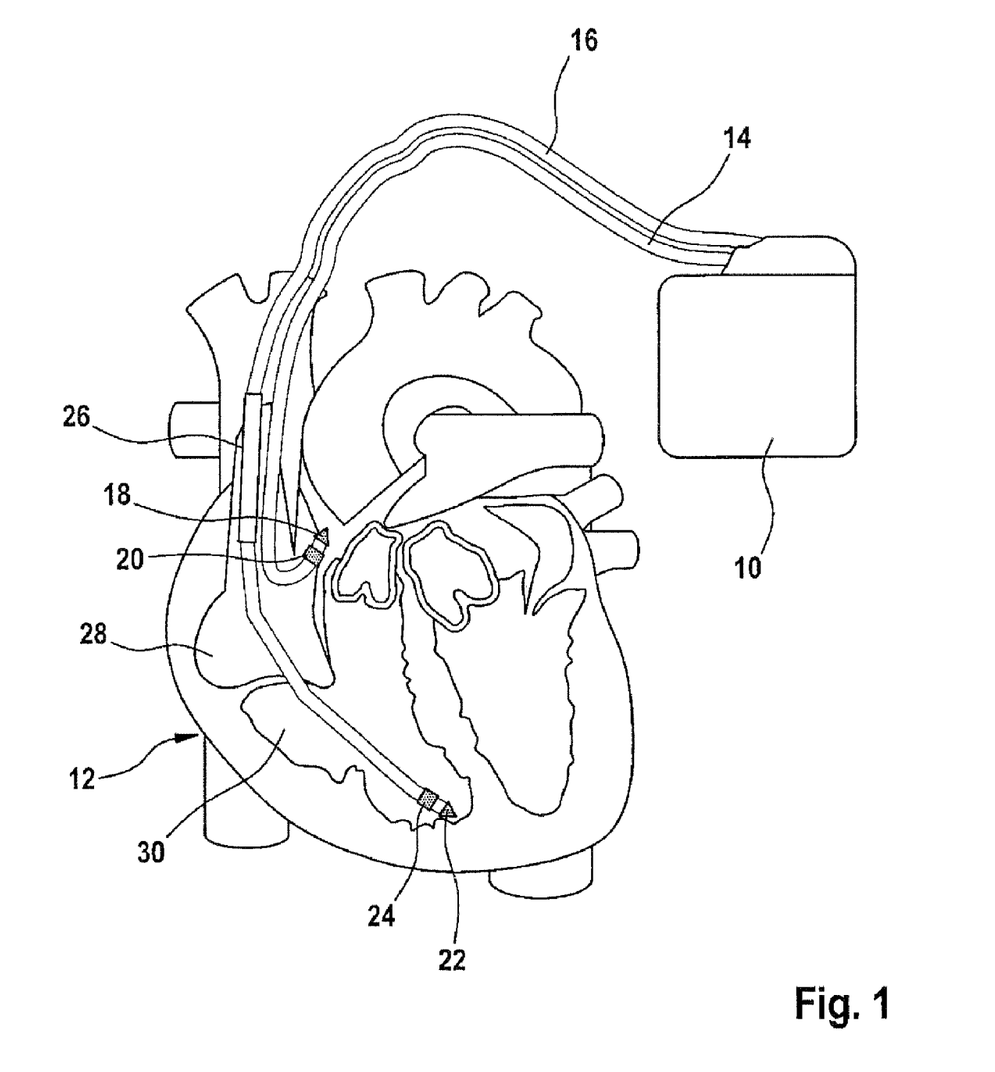
FIG. 1 shows a dual chamber pacemaker/atrial defibrillator connected to pacing/sensing leads placed in a heart.

Referring to FIG. 1, a dual chamber pacemaker/atrial defibrillator (implantable medical device, IMD) 10 connected to pacing/sensing leads placed in a heart 12 is illustrated. The IMD 10 is coupled to a heart 12 by way of leads 14 and 16, the lead 14 having a pair of right atrial electrodes 18 and 20 that are in contact with the right atrium 28 of the heart 12, and the lead 16 having a pair of electrodes 22 and 24 that are in contact with the right ventricle 30 of heart 12. Lead 16 furthermore carries an atrial shock electrode 26 placed in the right atrium.

The electrodes 18 and 22 are tip-electrodes at the very distal end of leads 14 and 15, respectively. Electrode 18 is a right atrial tip electrode RA-Tip and electrode 22 is a right ventricular tip electrode 22. Electrodes 20 and 24 are designed as ring electrode in close proximity but electrically isolated from the respective tip electrodes 18 and 22. Electrode 20 forms a right atrial tip electrode RA-Ring und electrode 24 forms a right ventricular ring electrode RV-Ring. Atrial shock electrode 26 is a coil electrode having a large surface compared to Tip- and Ring-electrodes 18 to 24.

Figure 2:
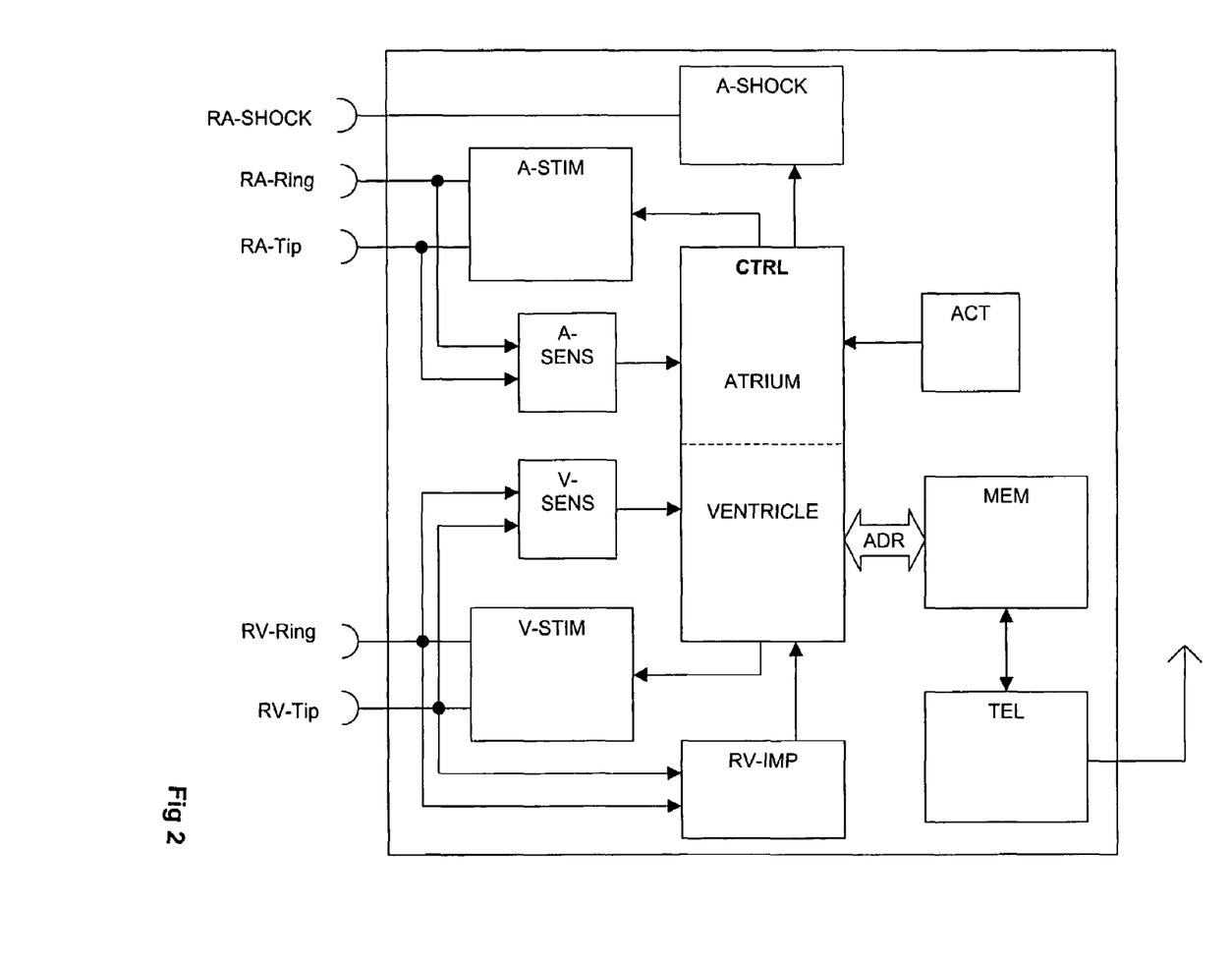
FIG. 2 shows a block diagram of the dual chamber pacemaker/atrial defibrillator from FIG. 1.

Referring to FIG. 2 a simplified block diagram of IMD 10 is illustrated. During operation, leads 14 and 16 are connected to respective output/input terminals of IMD 10 as indicated in FIG. 1 and carry stimulating pulses to the tip electrodes 18 and 22 from an atrial stimulation pulse generator A-STIM and a ventricular pulse generator V-STIM, respectively, or atrial defibrillation shocks from an atrial defibrillation shock generator A-SHOCK to coil 26. Further, electrical signals from the atria are carried from the electrode pair 18 and 20, through the lead 14, to the input terminal of an atrial channel sense amplifier A-SENS; and electrical signals from the ventricles are carried from the electrode pair 22 and 24, through the lead 16, to the input terminal of a ventricular sense channel amplifier V-SENS.

The ventricular sense channel amplifier V-SENS forms a sensing stage for sensing of R-waves. Ventricular sense channel amplifier V-SENS comprises a bandpass-filter with a pass band between 15 and 80 Hertz. For more specific detection of the R-wave, the ventricular sense channel amplifier V-SENS may comprise further highpass-filter or a second bandpass-filter having a lower cut off frequency of 24 Hertz or a pass band from 24 to 80 Hz respectively. Thus, T-wave in the ventricular signal or almost completely filtered out leaving the R-waves as only major event of relatively large amplitude in the filtered signal. The output signal of the second band pass filter is used for the amplitude criterion to synchronize the atrial defibrillation shock with an R-wave.

Furthermore, those R-wave amplitude values coming from both band pass filters are stored in a memory MEM of IMD 10 for generating two mean amplitude values from said stored R-wave amplitude values. A control unit CTRL is adapted to only store those R-wave amplitude values in memory MEM which occur during a normal sinus rate. Control unit CTRL is further adapted to generate a mean amplitude value from said amplitude values stored in memory MEM and to store said mean amplitude value for further use as reference amplitude for discrimination of R-waves from T-waves for the purpose of synchronizing an atrial defibrillation shock with an R-wave.

A right ventricular impedance measuring unit RV-IMD is capable to determine mechanical contractions of the right ventricle via impedance plethysmography. Thus, control unit CTRL can verify ventricular contractions via impedance measuring RV-IMP.

Control unit CTRL is adapted to evaluate an actual intracardiac impedance signal by comparing said actual intracardiac impedance signal with a stored reference intracardiac impedance signal by calculating a difference area between an actual impedance signal and a stored reference impedance signal and to compare the difference area to a stored reference area, said stored reference area representing the area defined by the reference impedance signal. The reference impedance signal represents an average impedance signal sensed during an intrinsic ventricular contraction. Further reference impedance signals may stored representing an average impedance signal after ventricular stimulation.

For the purpose of reliable confirmation of a ventricular contraction and to avoid synchronization of the atrial defibrillation shock with a T-wave wrongly sensed as R-wave, control unit CTRL is adapted to evaluate the intracardiac impedance signal in a time window starting with a sensed or stimulated ventricular event (which in case of a sensed ventricular event should be an R-wave but also could be a T-wave wrongly sensed as R-wave) and ending after 30 ms (immediately prior to delivery of the atrial defibrillation shock) and to suppress delivery of an atrial defibrillation shock when the difference area is larger than 15% of the reference area.

Control unit CTRL is further connected to the sense amplifiers A-SENS and V-SENS and to the stimulation pulse generators A-STIM and V-STIM. Control unit CTRL receives the output signals from the atrial sense amplifier A-SENS and from the ventricular sense amplifier V-SENS. The output signals of sense amplifiers A-SENSE and V-SENSE are generated each time that a P-wave or an R-wave, respectively, is sensed within the heart 12.

Control unit CTRL comprises an fibrillation detector connected to the atrial sense amplifier A-SENS. The atrial fibrillation detector responds to a very high rate of atrial sensed events As having a small amplitude. If control unit CTRL by means of said atrial fibrillation detector determines the presence of an atrial fibrillation, control unit CTRL will observe the ventricular rate in order to determine whether the ventricular rate meets a preset rate stability criterion or not. If the ventricular rate is sufficiently stable, control unit CTRL will trigger an atrial defibrillation shock within 30 ms after the next sensed R-wave having an amplitude with a magnitude exceeding 60% of the magnitude of a referent amplitude.

In the case that the stability criterion for the ventricular rate or the amplitude criterion are not met, control unit CTRL the generate trigger signals that are sent to the ventricular stimulation pulse generator V-STIM in order to achieve a stimulated contraction of the ventricle to which an atrial defibrillation shock can be synchronized.

In the absence of an atrial fibrillation, control unit CTRL generates trigger signals that are sent to the atrial stimulation pulse generator A-STIM and the ventricular stimulation pulse generator V-STIM, respectively, for regular dual chamber pacing. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or a V-pulse is being delivered to the heart, the corresponding sense amplifier, A-SENS and/or R-SENS, is typically disabled by way of a blanking signal presented to these amplifiers from the control unit CTRL, respectively. This blanking action prevents the sense amplifiers A-SENS and V-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, memory circuit MEM of IMD 10 that is coupled to the control unit CTRL over a suitable data/address bus ADR allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in IMD 10. This telemetry circuit TEL is connected to the control unit CTRL by way of a suitable command/data bus. Telemetry circuit TEL allows for wireless data exchange between the IMD 10 and some remote programming or analyzing device which can be part of a centralized service center serving multiple pacemakers.

IMD 10 in FIG. 1 is referred to as an atrial defibrillator/dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENS, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENS, the ventricular stimulation pulse generator V-STIM, and corresponding portions of the control unit CTRL, are commonly referred to as the ventricular channel.

In order to allow rate adaptive pacing in a DDDR mode, IMD 10 further includes a physiological sensor ACT that is connected to the control unit CTRL of IMD 10. While this sensor ACT is illustrated in FIG. 2 as being included within IMD 10, it is to be understood that the sensor may also be external to IMD 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Figure 3:
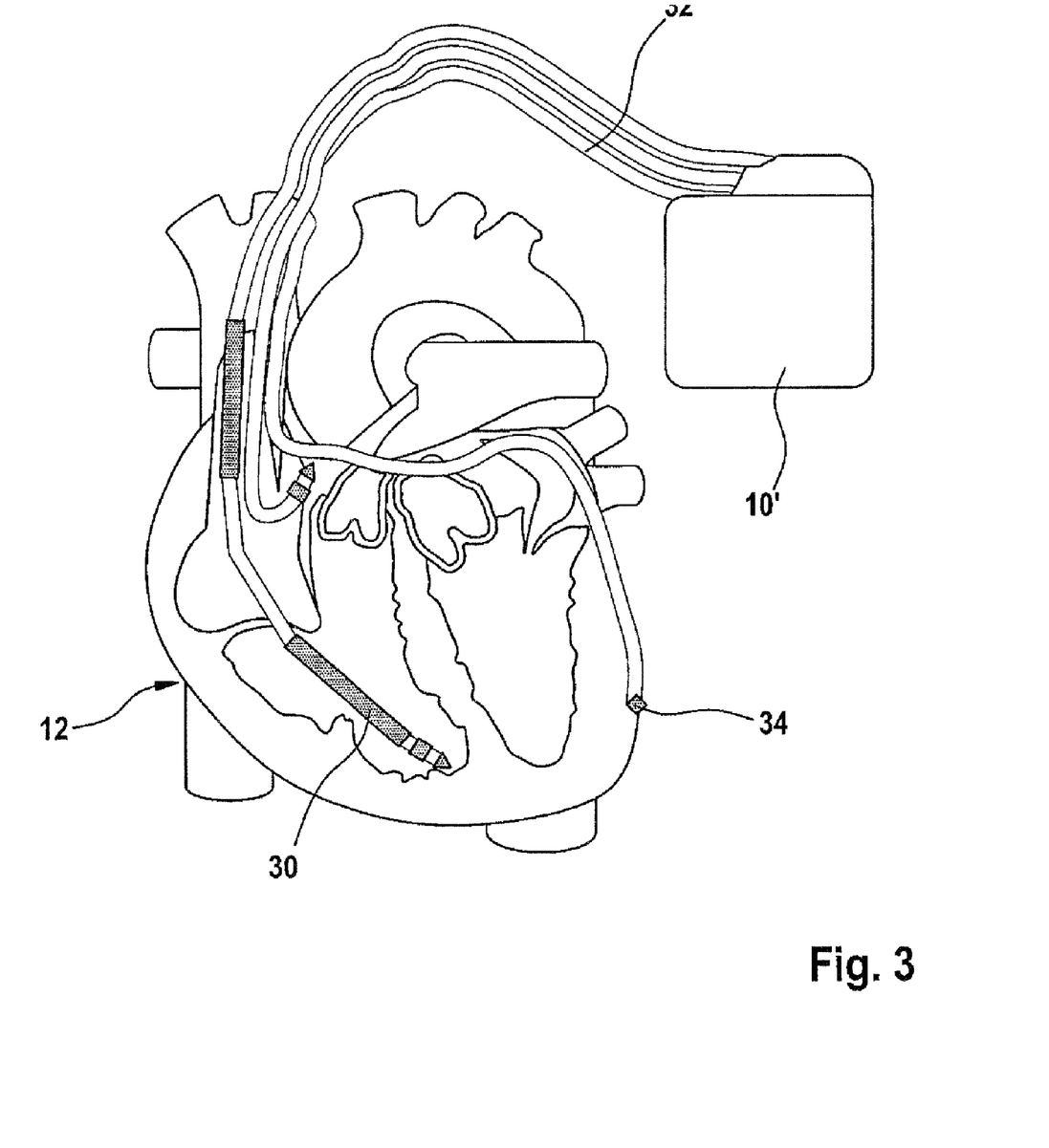
FIG. 3 shows biventricular pacemaker/atrial and ventricular defibrillator according to the invention.

FIG. 3 illustrates a full featured implantable medical device IMD 10' being a dual chamber, biventricular pacemaker and an atrial and ventricular defibrillator. For this purpose, a ventricular shock coil 30 is placed on ventricular electrode lead 16. In addition, a third electrode lead being a left ventricular electrode lead 32 is provided having a left ventricular tip electrode 34 at its distal end.

What is claimed:

1. An atrial defibrillator comprising:
   at least one stimulation pulse generator to generate pacing pulses for at least a ventricle of a heart;
   at least one sensing stage for sensing of intrinsic ventricular events, said intrinsic ventricular event being an R-wave having an amplitude;
   a defibrillation shock generator to generate an atrial defibrillation shock;
   an atrial fibrillation detector adapted to detect an atrial fibrillation;
   a control unit connected to the stimulation pulse generator, the sensing stage, the atrial fibrillation detector and the defibrillation shock generator, said control unit being adapted to trigger an atrial defibrillation shock after detection of an atrial fibrillation and synchronous with a sensed or a paced ventricular event,
   wherein
   the control unit is adapted to compare a sensed R-wave amplitude with a reference R-wave amplitude and synchronize an atrial defibrillation shock with either a paced ventricular event or a sensed ventricular event if said sensed ventricular event is an R-wave having an amplitude of at least 60% of the magnitude of the reference amplitude; and
   an impedance sensor connected to an impedance evaluation unit adapted to detect ventricular contractions by evaluating an intracardiac impedance signal, wherein the control unit is connected to the impedance evaluation unit and is adapted to evaluate an actual intracardiac impedance signal by comparing said actual intracardiac impedance signal with a stored reference intracardiac impedance signal, and wherein the control unit is adapted to form a difference area between an actual impedance signal and a stored reference impedance signal and to compare the difference area to a stored reference area, said stored reference area representing the area defined by the reference impedance signal.

2. The atrial defibrillator according to claim 1, additionally comprising a sensing stage adapted to sense atrial events and being connected to the atrial fibrillation detector.

3. The atrial defibrillator according to claim 2, wherein the sensing stage for sensing of intrinsic ventricular events comprises a band pass filter having a pass band between 15 Hz and 80 Hz.

4. The atrial defibrillator according to claim 3, wherein the sensing stage comprises a second filter having a lower cut-off frequency of 22 to 26 Hz for filtering a ventricular signal in order to suppress T-wave sensing.

5. The atrial defibrillator according to claim 4, wherein the control unit is adapted to synchronize an atrial defibrillation shock with a ventricular event sensed within a ventricular signal having passed the second filter.

6. The atrial defibrillator according to claim 1, wherein the sensing stage for sensing of intrinsic ventricular events comprises a band pass filter having a pass band between 15 Hz and 80 Hz.

7. The atrial defibrillator according to claim 6, wherein the sensing stage comprises a second filter having a lower cut-off frequency of 22 to 26 Hz for filtering a ventricular signal in order to suppress T-wave sensing.

8. The atrial defibrillator according to claim 7, wherein the control unit is adapted to synchronize an atrial defibrillation shock with a ventricular event sensed within a ventricular signal having passed the second filter.

9. The atrial defibrillator according to claim 8, wherein the control unit is adapted to trigger an atrial defibrillation shock within 30-100 ms after detection of an R-wave having an amplitude with a magnitude of at least 60% of the magnitude of the reference amplitude.

10. The atrial defibrillator according to claim 9, additionally comprising a memory for storing R-wave amplitudes sensed during episodes of sinus rate.

11. The atrial defibrillator according to claim 7, additionally comprising a memory for storing R-wave amplitudes sensed during episodes of sinus rate.

12. The atrial defibrillator according to claim 11, wherein the control unit is connected to the memory and is adapted to generate a mean amplitude value from R-wave amplitude values stored in said memory and to set said mean value as a reference amplitude.

13. The atrial defibrillator according to claim 12, wherein the memory for storing R-wave amplitudes is operationally connected to the second filter for filtering the R-wave amplitude to be stored in said memory.

14. The atrial defibrillator according to claim 1, wherein the control unit is adapted to evaluate an intracardiac impedance signal in a time window starting with a sensed ventricular event (R-wave) and ending after 30 to 50 ms and to suppress delivery of an atrial defibrillation shock when the difference area is larger than 10 to 20% of the reference area.

15. The atrial defibrillator according to claim 14, wherein the control unit is adapted to suppress delivery of an atrial defibrillation shock when the difference area is larger than 15% of the reference area.

16. The atrial defibrillator according to claim 1, wherein the control unit is adapted to trigger an atrial defibrillation shock within 30-100 ms after detection of an R-wave having an amplitude with a magnitude of at least 60% of the magnitude of the reference amplitude.

17. The atrial defibrillator according to claim 16, additionally comprising a memory for storing R-wave amplitudes sensed during episodes of sinus rate.

* * * * *

UNITED STATES PATENT AND TRADEMARK OFFICE
CERTIFICATE OF CORRECTION

PATENT NO.         : 7,532,928 B2
APPLICATION NO. : 11/354713
DATED                 : May 12, 2009
INVENTOR(S)       : Lang It is certified that error appears in the above-identified patent and that said Letters Patent is hereby corrected as shown below:

The drawing sheet, consisting of Fig. 3, should be deleted to be replaced with the drawing sheet, consisting of Fig. 3, as shown on the attached page.

Signed and Sealed this

Eighteenth Day of August, 2009

David J. Kappos
*Director of the United States Patent and Trademark Office*

Fig. 3